United States Patent [19]

Carrico, Jr. et al.

[11] Patent Number: 5,346,831
[45] Date of Patent: Sep. 13, 1994

[54] CYTORICH PROCESS SYSTEM

[75] Inventors: Charles L. Carrico, Jr.; William A. Fox, both of Burlington; James W. Geyer; Ernest A. Knesel, Jr., both of Greensboro, all of N.C.

[73] Assignee: Hoffman-La Roche Inc., Nutley, N.J.

[21] Appl. No.: 112,001

[22] Filed: Aug. 30, 1993

Related U.S. Application Data

[63] Continuation-in-part of Ser. No. 953,036, Sep. 29, 1992, abandoned.

[51] Int. Cl.$^5$ .............................................. G01N 1/00
[52] U.S. Cl. ...................................... 436/174; 436/46; 436/63; 422/57
[58] Field of Search .................. 436/63, 175, 46, 174; 422/57; 435/30

[56] References Cited

U.S. PATENT DOCUMENTS 3,764,215 10/1973 Wallach ............................. 356/36
4,688,513 8/1987 Eberle ................................. 118/52

OTHER PUBLICATIONS

Boon, et al., "Routine Cytological Staining Techniques," pp. 110–117 (1986).
Hutchinson, M. L., et al., Anatomic Pathology, vol. 96, No. 3, pp. 330–305 (1991).
Otto, K., et al., The Journal of Histochemistry and Cytochemistry, vol. 27, No. 1, pp. 14–18 (1979).

Primary Examiner—James C. Housel
Assistant Examiner—Lien Tran
Attorney, Agent, or Firm—George M. Gould; George W. Johnston; John P. Parise

[57] ABSTRACT

A process for producing a monolayer of cytological material on an optically-clear, cationically-charged substrate, includes the steps of separating the cytological material by centrifugation over a density gradient, producing a packed pellet of the cytological material, mixing the pellet of the cytological material, withdrawing an aliquot of a predetermined volume of the material from the mixed pellet of the cytological material, depositing the aliquot and a predetermined volume of water into a sedimentation vessel, which is removably secured to the substrate, allowing the cytological material to settle onto the substrate under the force of gravity, and after settlement of the cytological material, removing the water from the sedimentation vessel.

11 Claims, No Drawings

CYTORICH PROCESS SYSTEM

CROSS-REFERENCE TO PRIOR APPLICATIONS

This application is a continuation-in-part of Ser. No. 07/953,036, filed Sep. 29, 1992, now abandoned.

FIELD OF THE INVENTION

The invention is directed to a method for producing a monolayer of cytological material on an optically-clear, cationically charged substrate.

BACKGROUND OF THE INVENTION

Conventional cellular smears collected on site by a clinician are unsuitable for automated screening using image analysis techniques due to variable thickness and cell overlap. A standardized and well-controlled specimen preparation procedure is necessary for quantitative analyses, such as in image cytometry. Dispersion of large cellular aggregates, optimal cellular preservation, and effective, efficient transfer of the cellular material to a slide are all requirements for quantitative analysis.

Advances in image analysis technology now make it possible to use an automated prescreening system for conventionally prepared cervical smears. One approach uses an automated system to identify a large proportion of normal cervical smears without human interaction. Other smears are referred to a cytotechnologist for standard manual screening. Although automation allows normal specimens to be completely removed from the manual workload, for such a system to be clinically useful, it should not increase the rate of false negative diagnoses.

Automated analysis of cytological material can be optimized by preparing monolayers of cells on the specimen slides. Previously, many methods have been used to produce a "monolayer" of cells on a specimen slide. A "monolayer" is defined as a substantially two-dimensional layer of uniformly distributed cellular material, predominantly made up of single cells and small clusters of cells, on a glass specimen slide or other substrate, without substantial folding or overlapping of cells. Preparation of a monolayer facilitates observation of cellular abnormalities, as compared to slides prepared using conventional smear techniques. Previous methods for producing monolayers include ultrasonic vibration, shearing with a rotor, syringing, forced filtration, centrifugation, sedimentation, and filter transfer. Unfortunately, these methods are unsuitable for automation, since detection is hindered by cell-folding, cell overlap, and distorted morphology.

An automated technique has been developed which is called "ThinPrep" (Cytec Corporation, Marlborough, Mass.). The technique is described by Hutchinson, M.L., et al., Anatomic Pathology, Vol. 96, No. 3, pp. 300–305 (1991), and involves using a disposable hollow cylinder, which contains a polycarbonate filter bonded to the base. The cylinder-filter assembly is inserted into a vial containing a cellular suspension. Cells are then dispersed by rotating the cylinder at high speed. A variable volume of suspension is drawn into the cylinder, thereby attracting cells onto the outer surface of the filter. After 40,000 to 50,000 cells are collected onto the filter, the cylinder is removed from the vial and inverted. The filtrate is then aspirated from the cylinder, and the cells touch-transferred to a glass specimen slide. This procedure produces non-optimal cell dispersion cell overlap, and cell folding occurs. The automated device prepares slides one at a time and must complete a slide before going on to the next slide.

SUMMARY OF THE INVENTION

The invention relates to a method for producing a monolayer of cytological material on a cationically-charged substrate. The method comprises the steps of separating the cytological material by centrifugation over a density gradient, producing a packed pellet of the cytological material, mixing the pellet of the cytological material, withdrawing an aliquot of a predetermined volume from the mixed pellet, depositing the aliquot and a predetermined volume of water into a sedimentation vessel, which is removably secured to the cationically-charged substrate, allowing the cytological material to settle onto the substrate under the force of gravity, and after settlement of the cytological material, removing the water from the sedimentation vessel. For automated analysis, the sedimentation vessel may be detached from the substrate.

DETAILED DESCRIPTION OF THE INVENTION

The invention will now be discussed in terms of its preferred embodiments. These embodiments are set forth to aid in the understanding of the invention, but are not to be construed as limiting.

The invention is directed to a method for producing a monolayer of cytological material on a cationically-charged substrate. Sample vials received from a physician's clinic typically contain a sample in about 10 mL alcohol/saline preservative. The sample is prepared for centrifugation by disaggregating the clumps or clusters of cells in the sample vial. Such disaggregation may be by any methods known in the art, such as syringing, trypsinizing, ultrasonication, shaking, vortexing, or by use of the device described in copending U.S. Pat. application Ser. No. 07/953,035, filed Sep. 29, 1992, the contents of which are herein incorporated by reference.

The sample is centrifuged over a density gradient to separate the debris and artifacts from clinically significant material to be analyzed. The choice of density gradient and spin speed is readily determined by one skilled in the art based on the type of cells to be isolated. Examples of gradients include, but are not limited to, starch solutions, such as herastarch ("Hespan"), O-(2-hydroxyethyl)-aminopectin-hydrosylate ("Plasmasteril"), or Percoil. Guidelines suitable for use with cervical samples are found in Otto, K., et al., J. Histochem. and Cytochem., 27(1):14–18 (1978), the contents of which are herein incorporated by reference. After a final high force spin, supernatant is decanted, leaving a packed pellet of cells at the bottom of the centrifuge tube. Sample vials may vary greatly in the total number of cells contained. However, cells or pellets produced by centrifugation will contain approximately the same cell concentration per unit volume of pellet after mixing to homogeneity (such as by vortexing, typically with the addition of a known volume of fluid). That is, even though one sample vial contains for example, 1,000,000 cells, and another vial contains 2,000,000 cells, after centrifugation and homogenization, the cell concentration between similarly processes cell pellets will be essentially identical. By "essentially identical" it is meant that the cell concentrations are within tolerances acceptable to the cytologist.

To ensure uniformity of cells, the pellet is mixed. Numerous methods of mixing cells to a homogeneous suspension are known in the art, e.g., vortexing, syringing etc., and will not be discussed in detail. To aid in mixing, a predetermined amount of water may be added. As used herein, the term "water" is to include dilutents such as water and other aqueous solutions. Currently the preferred water is pure distilled deionized water. However, solutions such as normal saline, phosphate buffered saline, TRIS buffer, etc. may be preferred under given conditions. Therefore, to produce uniform and consistent monolayers from sample to sample, an aliquot of a predetermined volume of cell pellet is withdrawn, mixed with water, and deposited into a sedimentation vessel. The volume of the aliquot withdrawn from the cell pellet is typically between about 25 and about 500 $\mu$L, and is more preferably about 150 $\mu$L, for an area of about 132 mm$^2$ to be covered on the slide. It is currently preferred to have approximately 20,000 to 40,000 cells fixed to the slide in an area of about 132 mm$^2$. Each aliquot should contain approximately the same number of cells as subsequent samples, having the same aliquot volume. The cell aliquot is preferably mixed with deionized water in a volume of about 500 $\mu$L. The exact volume of water used is not critical, since excess water may be aspirated off later during the procedure.

The cell aliquot and water aliquot are transferred to a sedimentation vessel which is removably attached to a microscope slide (preferably optically clear). The type of sedimentation vessel is not of paramount concern. However, it is preferred that the vessel have an open top end for receiving the cells and water, and an open bottom end which abuts the surface of the microscope slide. The vessel, preferably cylindrical in shape, is secured to the microscope slide and is capable of containing the liquid and cell contents without leakage. Typical sedimentation vessels include that described in U.S. Pat. No. 4,688,513, and that described and claimed in copending U.S. Pat. application Ser. No. 07/953,037, filed Sep. 19, 1992, the contents of both are herein incorporated by reference. Once transferred to the sedimentation vessel, cells are allowed to settle for approximately 10 minutes onto a cationically charged microscope slide. The cationic charge attracts and holds the negatively-charged cells to the slide surface. The slide may be cationically-charged in any conventional manner, but preferably is coated with Poly-L lysine, as is well-known in the art.

It will be appreciated that the volume of the aliquot from the cell pellet is dependent on the size of total area to be coated, and on the charge-capacity of the coated substrate. Knowing the above description of the aliquot volumes and the final fixed cell concentration per area of slide, it is within the skill in the art to calculate the optimal cell pellet aliquot necessary to deposit using any given cationic coating material. Settling of the cells onto the slide occurs under the force of gravity, and is not assisted through centrifugation to avoid cell overlap, folding, and distorted cell morphology. During settling, negatively-charged cells will repel one another and will be attracted to the cationically-charged slide until the slide has been substantially covered with a monolayer of cells. Excess cells may be aspirated along the supernatant. The sedimentation vessel is then removed and the deposited cells may be treated for Pap-staining in a conventional manner.

The following example is intended to illustrate the subject method, but is not intended to limit its scope.

EXAMPLE

Receiving Sample

A vial containing 10 ml alcohol/saline preservative and patient cells is received from the physicians' office. Each patient sample is assigned a daily sequence number (1,2,3,etc.). The daNg number is placed on the vial, worksheet, and all corresponding tubes and slides for that patient.

Sample Preparation

The sample is prepared for centrifugation by first disaggregating the clumps or clusters of cells in the sample vial. Such disaggregation may be effected by methods known in the art, such as syringing, trypsinizing, ultrasonication, shaking, vortexing, or by use of the device described in copending U.S. Pat. application Ser. No. 07/953,035, filed Sep. 29, 1992, the contents of which are herein incorporated by reference. After disaggregation, the patient sample is drained completely and layered over a density gradient in a 12 ml conical tube. Any density gradient may be used. However, the preferred density gradient is a plasma expander material comprising 6% betastarch solution, and 0.9% physiological saline, also known by the tradename "Hespan" made by NPBI, Emmer-Compascuum, the Netherlands.

Sample Centrifugation

Place 12 ml conical tubes containing density gradient and sample cells into centrifuge buckets, balance and centrifuge for 5 minutes, at a force of about 600G. Then aspirate the liquid down to the 5 ml mark on the conical tube. Remove the centrifuge buckets and centrifuge the 12 ml conical tube with remaining liquid for 10 minutes, at 800G. Decant the tubes for approximately 10 seconds and blot on a paper towel, tapping lightly 2 or 3 times at a 45 degree angle. The tubes now contain packed cells of varying volumes. Upon mixing to homogeneity, the pellets generally contain the same concentration of cells per unit volume of liquid.

Sample Handling and Staining

After the final spin after decanting, add 50 $\mu$l of deionized H$_2$O, and mix the sample by syringing 5 times through a 0.042 inch tip. Upon completion of mixing, dispense 150 $\mu$l of sample followed by 500 $\mu$l of deionized H$_2$O into a sedimentation vessel attached to a slide which has been conventionally coated with Poly-L lysine (1% Sigma). The transferred sample is allowed to settle within the vessel for approximately 10 minutes. The excess sample is aspirated off and the chamber rinsed with 2 ml deionized H$_2$O two times (aspirating between each addition). Histological grade alcohol (2 ml) is added to the sedimentation chamber. A standard Papanicolaou stain is then performed on the slide.

It will become apparent to those skilled in the art that the method described above can be varied without departing from the scope and spirit of the invention. The scope of the invention is only tube limited by the claims which follow and their equivalents.

What is claimed is:

1. A method for preparing a monolayer of a cytological material on a cationically-charged substrate, which comprises the steps of:

(a) separating the cytological material by centrifugation over a density gradient;

(b) producing a packed pellet of the cytological material;
(c) mixing the pellet of the cytological material;
(d) withdrawing an aliquot of a predetermined volume from the mixed pellet of the cytological material;
(e) depositing the aliquot in a predetermined volume of water into a sedimentation vessel having a base, which vessel is removable secured to the cationically-charged substrate;
(f) allowing the cytological material to settle onto the substrate under the force of gravity without flow of the aliquot and the water from the base of the sedimentation vessel;
(g) after settlement of the cytological material, removing the water from the sedimentation vessel.

2. The method of claim 1, wherein the separating comprises centrifuging the cytological material at a force of about 600G over a density gradient comprising 6% hetastarch solution.

3. The method of claim 1, wherein producing a packet pellet comprises centrifuging the cytological material at a force of about 800G over a density gradient comprising 6% hetastarch solution.

4. The method of claim 1, wherein withdrawing the aliquot of a predetermined volume comprises withdrawing approximately 150 $\mu$L of the mixed pellet.

5. The method of claim 1, wherein the depositing comprises mixing the aliquot of cytological material with approximately 500 $\mu$L of water.

6. The method of claim 1, wherein the depositing is to the substrate comprising a glass microscope slide.

7. The method of claim 1 further comprising staining the cytological material within the sedimentation vessel after settlement of the cytological material.

8. The method of claim 7, wherein the staining comprises applying a Papanicolaou stain.

9. The method of claim 1, wherein the mixing of the pellet of the cytological material further comprises adding thereto a predetermined volume of water.

10. The method of claim 9, wherein the predetermined volume of water added during mixing is approximately 50 $\mu$L.

11. The method of claim 1 further comprising detaching the sedimentation vessel from the substrate.

* * * * *